US00PP15904P3

(12) United States Plant Patent
Houbraken

(10) Patent No.: US PP15,904 P3
(45) Date of Patent: Aug. 2, 2005

(54) ***ARGYRANTHEMUM FRUTESCENS* PLANT NAMED 'ARGYDOWITIS'**

(50) Latin Name: *Argyranthemum frutescens*
Varietal Denomination: Argydowitis

(75) Inventor: AnneMarie Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 103 days.

(21) Appl. No.: 10/706,774

(22) Filed: Nov. 12, 2003

(65) Prior Publication Data

US 2005/0102725 P1 May 12, 2005

(51) Int. Cl.[7] ..... A01H 5/00

(52) U.S. Cl. ..... Plt./263

(58) Field of Search ..... Plt./263

*Primary Examiner*—Anne Marie Grunberg

(74) *Attorney, Agent, or Firm*—Edouard G. Lebel

(57) ABSTRACT

A distinct cultivar of Marguerite Daisy plant named 'Argydowitis' characterized by its upright vigorous plant habit, good field performance, large semi-double white flowers, dark green colored leaves, freely flowering with numerous inflorescences per plant.

1 Drawing Sheet

Latin name of the genus and species of the plant claimed: *Argyranthemum frutescens.*
Varietal denomination: 'Argydowitis'.

BACKGROUND OF THE INVENTION

The present invention relates to a new and distinct cultivar of Marguerite Daisy plant, botanically known as *Argyranthemum frutescens* and referred to by the cultivar name 'Argydowitis'. The new cultivar is a product of a planned breeding program conducted by the inventor in Enkhuizen, The Netherlands. The objective of the breeding program was to develop a more vigorous plant that flowers early with a good field performance during the whole summer.

DESCRIPTION OF THE DRAWING

This new Marguerite Daisy plant is illustrated by the accompanying photographic drawing which shows blooms, buds and foliage of the plant in full color, the color shown being as true as can be reasonably obtained by conventional photographic procedures (FIG. 2). The depicted plant is of the same age as disclosed in the botanical description.

The dimensions of the florets of this new Marguerite Daisy are illustrated more precisely by the accompanying photographic drawing which shows the florets next to a ruler (FIG. 1).

DESCRIPTION OF THE NEW CULTIVAR

The following detailed descriptions set forth the distinctive characteristics of this new Marguerite Daisy plant. The data which defines these characteristics were collected from asexual reproductions carried out in Enkhuizen, The Netherlands. The plant history was taken on 20 weeks old plants, grown in the greenhouses in Enkhuizen, The Netherlands with day temperatures ranging from 12 to 18 degree C., and night temperatures ranging from 10 to 14 degrees Celsius.

Color references are primarily to The R.H.S. Colour Chart of The Royal Horticultural Society of London where general terms of ordinary dictionary significance are used.

The plant:
Classification
Botanical.—*Argyranthemum frutescens*'Argydowitis'.
Parentage:
*Female parent.*—Properietary seedling selection of *Argyranthemum frutescens*, identified as number 'A 40-1' (unpatented). Breederscode of the new plant is 'C 45-6'.
*Male parent.*—Unidentified selection of *Argyranthemum frutescens.*
Propagation:
*Type cuttings.*—Terminal cuttings.
*Time to initiate roots.*—7 to 10 days at air temperature of 21 degree C.
*Time to develop roots.*—7 to 14 days at air temperature of 18 degree C.
Plant description:
*Growth habit.*—Upright.
*Plant height.*—25–28 cm.
*Vigor.*—Vigorous.
*Spreading area of plant.*—25–30 cm.
*Strength.*—Very good.
*Branching character.*—Freely branching, plants do not require pinching.
*Crop time.*—About 10 weeks are required to produce a finished flowering plant in a 10.5 cm container from a good developed cutting.
The stem:
*Diameter.*—4 mm.
*Shape.*—Round, bit grooved.
*Anthocyan pigmentation.*—Absent.
*Length of internode.*—1.5–2.5 cm.
*Pubescence.*—Absent.
*Color.*—143C.

The foliage:

*Arrangement*.—Alternate.
*Shape of leaf*.—Bipinnatisect.
*Leaf apex*.—Acute.
*Leaf base*.—Attenuate.
*Texture*.—Thick glabrous smooth.
*Length*.—6–7 cm.
*Width*.—3–3.5 cm.
*Depth of incision=margin*.—Laciniate.
*Color relating to both juvenile and mature leaves*.—Upper side: 133A–139A. Lower side: 138B.
*Pubescens*.—Absent.
*Petiole*.—Absent.
*Venation*.—Shape: Pinnate. Color: 138A.

The flower bud:

*Peduncle*.—Length: 6–10 cm. Strength: Strong. Texture: Smooth. Color: 144A.
*Size bud*.—Diameter: 4–7 mm. Length: 4–5 mm.
*Shape flower bud*.—Flattened, round.
*Color bud*.—163C.

Inflorescence:

*Diameter*.—4.2–5.0 cm.
*Form*.—Capitula with 2 series of ray florets and 10–15 series of grown disc florets, which give the semi double impression.
*Receptacle height*.—0.5 cm.
*Involucre/phyllaries*.—3 series of 5 bracts, tightly to receptacle. Shape: Elliptic, with broad apex. Margin: Entire. Length: 2–3 mm. Color: Upper: 143A. Lower: 143A.
*Fragrance*.—Absent.
*Quantity of inflorescences*.—±60–100 flowers/plant depending on age and growing conditions.
*Flowering period*.—April till October in N-W Europe, plants flower continuously during this period.
*Lastingness of blooms*.—7–10 days.

Ray florets:

*Shape of ray florets*.—Ligulate.
*Apex*.—Rounded, little incised.
*Base*.—Cordate.
*Margin*.—Entire.
*Color*.—155C.
*No. of ray florets per inflor*.—22–26.
*Size of the ray floret*.—Length: 1.4–1.7 cm. Width: 0.4–0.7 cm.
*Texture*.—Smooth.

Disc florets:

*Shape of disc florets*.—Tubular (trumpet shape) with 5 lobes.
*Color*.—12A.
*Diameter of disc floret*.—Young: 1 mm. Old: 3 mm.
*Number of disc florets/flower*.—±80.

Androecium:

*Anther color*.—Yellow 15A.
*Pollen color*.—Yellow 15A.
*Amount of pollen*.—Only in disc florets little pollen.

Gynoecium:

*Pistil number*.—One per floret (ray florets only).
*Pistil length*.—About 2 mm.
*Style color*.—Yellow green 144D.
*Style length*.—About 2 mm.
*Stigma color*.—Yellow orange 14A.
*Stigma shape*.—Bilobed.
*Ovary color*.—144C.

Disease resistance: No susceptibility nor resistance to fungal, bacterial or viral pathogens has been noted. Material is free of virus and *Chrysanthemum* stunt viroid (CSVd).

Seed: Seed production is not observed.

Physiological and ecological characteristics: Comparison with 'Sugar Button' and 'Argydowitis' on characteristics in which the new plant differs:

| | 'Sugar Button' (PP 11,980) | 'Argydowitis' |
|---|---|---|
| Plant height | 19–22 cm | 25–28 cm |
| Plant habit | compact | upright |
| Flower diameter | 3.0–3.5 cm | 4.2–5.0 cm |
| Foilage color | 137A–137B | 133A–139A |

No description on parental lines available. Material no longer exists as such.

What is claimed is:

1. A new and distinct variety of *Argyranthemum* plant, substantially as herein illustrated and described, characterized particularly as to novelty by its vigorous but sturdy upright plant habit with continuous flowering during the season, large semi-double white flowers and dark green foliage, flowering the whole summer.

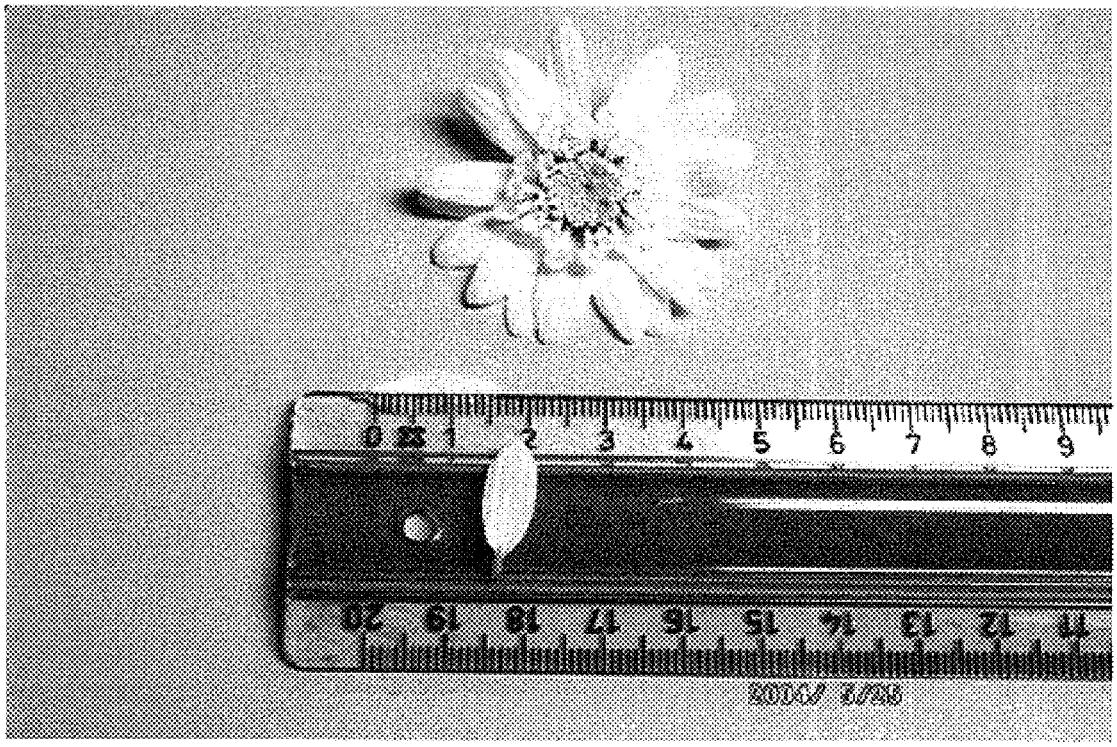
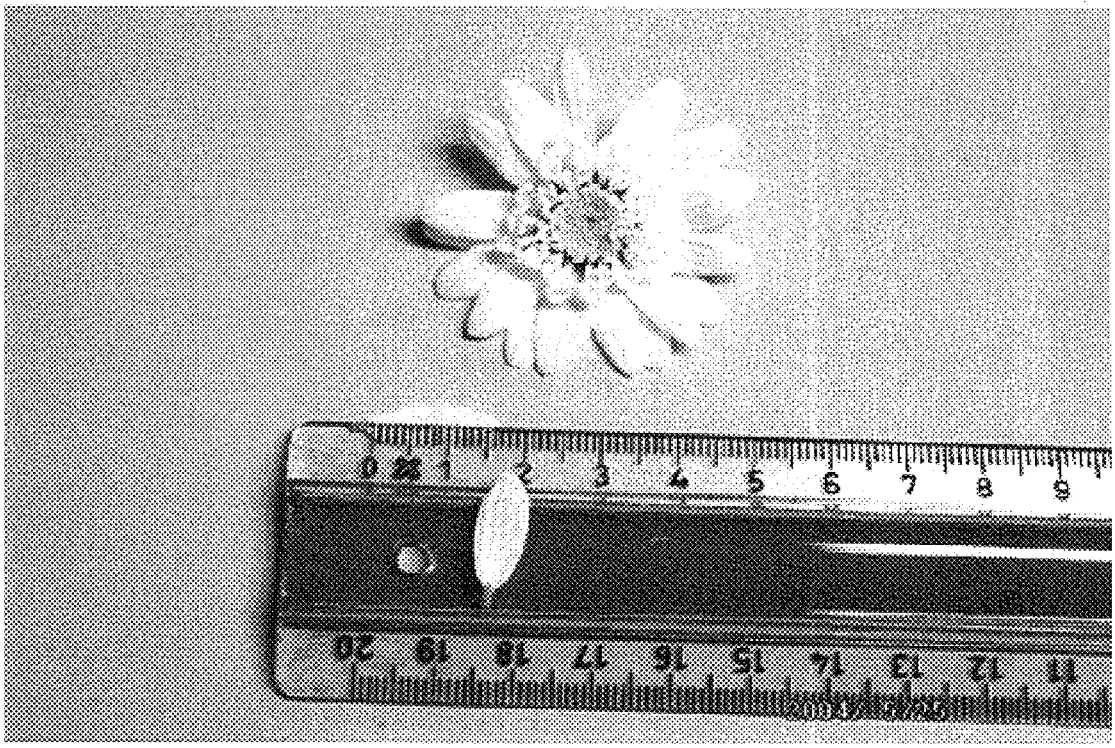

* * * * *